United States Patent
Clark et al.

(10) Patent No.: US 10,774,089 B2
(45) Date of Patent: Sep. 15, 2020

(54) METHOD FOR PRODUCING LEVOGLUCOSENONE

(71) Applicant: University of York, York (GB)

(72) Inventors: James Hanley Clark, York (GB); Mario De Bruyn, York (GB); Vitaliy Lvovich Budarin, York (GB)

(73) Assignee: UNIVERSITY OF YORK (GB)

( * ) Notice: Subject to any disclaimer, the term of this patent is extended or adjusted under 35 U.S.C. 154(b) by 0 days.

(21) Appl. No.: 15/567,639

(22) PCT Filed: Apr. 20, 2016

(86) PCT No.: PCT/GB2016/051095
§ 371 (c)(1),
(2) Date: Oct. 19, 2017

(87) PCT Pub. No.: WO2016/170329
PCT Pub. Date: Oct. 27, 2016

(65) Prior Publication Data
US 2018/0111947 A1 Apr. 26, 2018

(30) Foreign Application Priority Data

Apr. 20, 2015 (GB) .................................. 1506701.0
May 27, 2015 (GB) .................................. 1509131.7

(51) Int. Cl.
| | | |
|---|---|---|
| *C07D 493/08* | (2006.01) | |
| *C10B 53/02* | (2006.01) | |
| *C10L 9/08* | (2006.01) | |
| *C12P 19/02* | (2006.01) | |
| *C12P 19/14* | (2006.01) | |
| *C13K 1/02* | (2006.01) | |

(52) U.S. Cl.
CPC ............ *C07D 493/08* (2013.01); *C10B 53/02* (2013.01); *C10L 9/083* (2013.01); *C12P 19/02* (2013.01); *C12P 19/14* (2013.01); *C12Y 302/01004* (2013.01); *C12Y 302/01008* (2013.01); *C13K 1/02* (2013.01); *C12P 2203/00* (2013.01); *Y02E 50/14* (2013.01); *Y02E 50/15* (2013.01)

(58) Field of Classification Search
CPC ..................................................... C07D 493/08
USPC ........................................................ 549/397
See application file for complete search history.

(56) References Cited

U.S. PATENT DOCUMENTS

| | | | |
|---|---|---|---|
| 2010/0044210 A1* | 2/2010 | Robinson ................. | C08H 8/00 204/157.68 |
| 2011/0219679 A1* | 9/2011 | Budarin ................... | C10B 19/00 44/605 |
| 2013/0172586 A1 | 7/2013 | Desilva et al. | |
| 2013/0172629 A1 | 7/2013 | Allgeier et al. | |
| 2013/0231505 A1 | 9/2013 | Allgeier et al. | |

FOREIGN PATENT DOCUMENTS

| | | | | |
|---|---|---|---|---|
| EP | 1978086 | * | 3/2008 | ............ C12M 1/107 |
| WO | 2008/098036 A1 | | 8/2008 | |
| WO | 2011/000030 A1 | | 1/2011 | |
| WO | 2011/149339 A1 | | 12/2011 | |
| WO | 2013/101970 A1 | | 7/2013 | |
| WO | 2013/163571 A2 | | 10/2013 | |

OTHER PUBLICATIONS

Sarotti, Green Chem., 2007, 9, 1137-1140.*
Sarotti, Green Chemistry, 2007, 1137-1140.*
Sarotti, Current Organic Synthesis, 2012,9,439-459.*
De bruyn, Energy Environ. Sci., 2016, 9, 2571.*
Fan, J. Am. Chem. Soc. 2013, 135, 11728-11731.*
Cecilia, "Possibilities of process intensification using microwaves applied to catalytic microreactors" Chem. Eng. Proc. vol. 46, Issue 9, pp. 870-881 (Sep. 2007).*
Wallance, Mar. 2013 Stellenbosch University http://scholar.sun.ac.za.*
Liu et al., "Selective Pyrolysis Behaviors of Willow Catalyzed via Phosphoric Acid," Advanced Materials Research, vols. 724-725, (2013), pp. 413-418.
Kawamoto et al., Catalytic pyrolysis of cellulose in sulfolane with some acidic catalysts, J Wood Sci (2007) 53:127-133.
Kudo et al., "Efficient levoglucosenone production by catalytic pyrolysis of cellulose mixed with ionic liquid," Green Chem., 2011, 13, 3306-3311.
Sarotti et al., "Recent Applications of Levoglucosenone as Chiral Synthon," Current Organic Synthesis, 2012, vol. 9, No. 4, 439-459.
Sherwood et al., "Dihydrolevoglucosenone (Cyrene) as a bio-based alternative for dipolar aprotic solvents," Chem. Commun., 2014, 50, 9650-9652.
PCT Written Opinion of the International Searching Authority for International Application No. PCT/GB2016/051095, dated Jul. 18, 2016, 5 pages.

* cited by examiner

*Primary Examiner* — Nizal S Chandrakumar
(74) *Attorney, Agent, or Firm* — K&L Gates LLP

(57) ABSTRACT

There is described a method of producing (−)-levoglucosenone, said method comprising, heating lignin to a temperature in excess of 150° C. for a time sufficient to convert a proportion of the lignin to (−)-evoglucosenone.

20 Claims, 1 Drawing Sheet

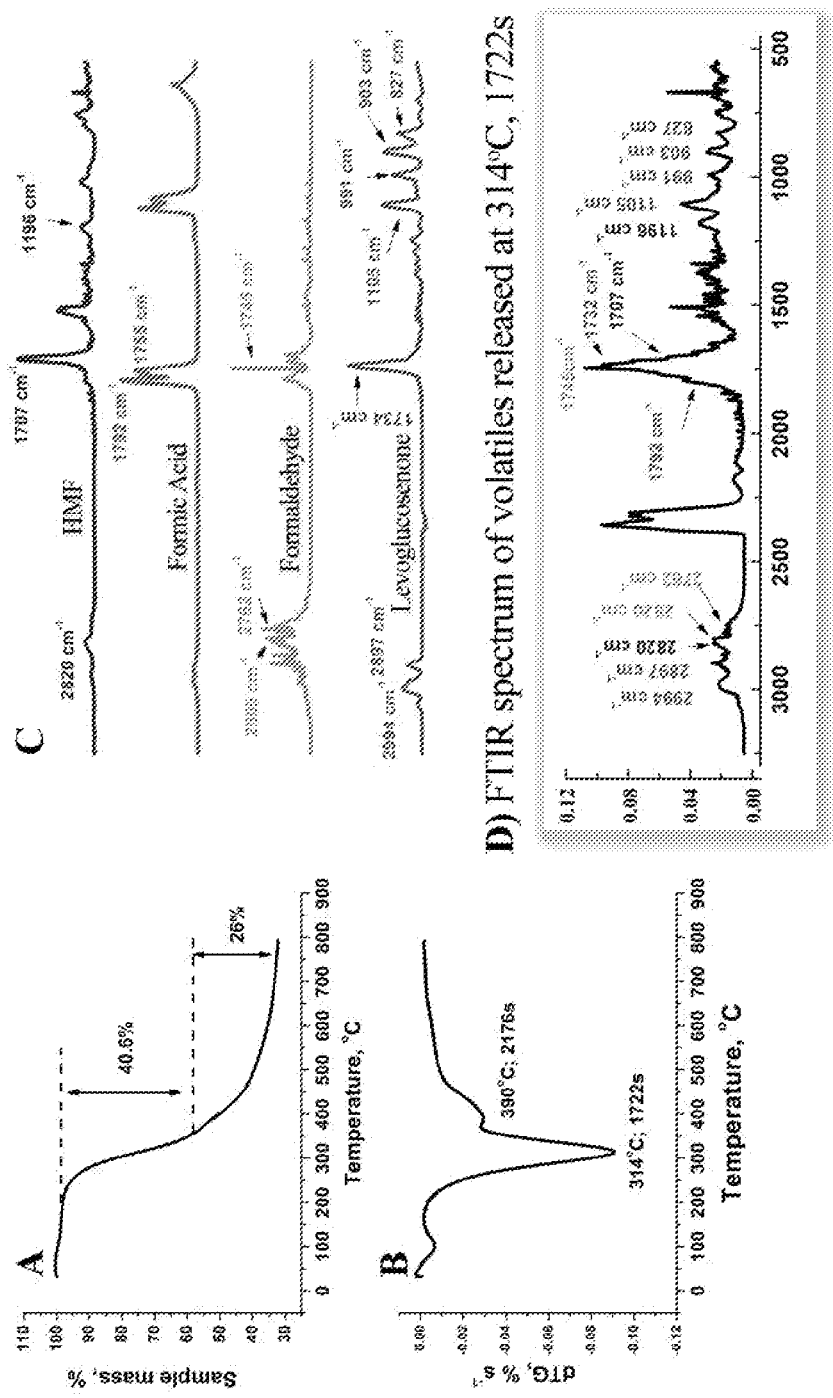
Figure 1. TG-IR analysis of waste lignin

METHOD FOR PRODUCING LEVOGLUCOSENONE

CROSS REFERENCE TO RELATED APPLICATIONS

This is the national phase under 35 U.S.C. § 371 of International Application No. PCT/GB2016/051095, filed on Apr. 20, 2016, which claims priority to and the benefit of United Kingdom Patent Application Nos. 1506701.0, filed on Apr. 20, 2015 and 1509131.7, filed on May 27, 2015, the entire disclosures of each of which are incorporated by reference herein.

FIELD OF THE INVENTION

The present invention relates to a method for producing levoglucosenone.

More particularly, the present invention relates to a method of thermochemical treatment of lignocellulosic materials so that they are converted to a mixture of volatile organic compounds including levoglucosenone, water and acid hydrolysis lignin.

BACKGROUND OF THE INVENTION

In this specification, where a document, act or item of knowledge is referred to or discussed, this reference or discussion is not an admission that the document, act or item of knowledge or any combination thereof was at the priority date:
 (i) part of common general knowledge; or
 (ii) known to be relevant to an attempt to solve any problem with which this specification is concerned.

With world crude and petroleum oil prices being normally fairly volatile, due to a wide variety of market and politically related supply & demand factors, the more expensive oil production from these unconventional sources is economically uncertain. Furthermore, the production of oil and its transport, as well as the combustion of petroleum-derived fuels in internal combustion engines, is a major source of $CO_2$, $CH_4$ and $NO_x$ production. These are classified as greenhouse gases, i.e. gases that trap heat in the atmosphere, which are responsible for the global climate change. To alleviate these concerns significant effort has been devoted to the production of fuels from renewables. Thereby the term renewables refers generally to lignocellulosic materials, i.e. biomass derived mainly from higher plants or its processed residues (e.g. paper, pulp, lignin waste), and its components being cellulose, hemicellulose and lignin.

The conversion of biomass into fuels is commonly practised in biorefineries. The UK's National Non-Food Crops Centre (NNFCC) defines a biorefinery as a manufacturing site involved in the refining of biomass material to yield purified materials and molecules. This conversion can be achieved using biological or thermochemical processing or a mixture of both. The fuel or fuel additives produced by biorefineries concern bio-alcohols such as bioethanol and biobutanol. First generation biorefineries derive these from starchy products, such as corn kernels, because starches are easy to break down into the sugars needed to make bio-alcohols.

Over recent years, concern on the use of food-for-fuel has shifted attention to second generation biorefineries which use non-food lignocellulosic material. These contain tough cellulose fibres which are much harder to process and break down into fermentable sugars. The production of bio-alcohols from lignocellulosic biomass for fuel applications presents a number of financial challenges due to low profit margins. Also, second generation biorefineries produce substantial amounts of waste lignin for which no ready high-value applications are known.

Waste lignin is defined as lignin-rich solid residues remaining after industrial high-temperature pre-treatment, with or without the presence of mineral acids, which deconstructs the densely packed cellulose fibres to bundles of polysaccharide chains that are more accessible to enzymatic hydrolysis. This pre-treatment is generally conducted at elevated temperature which is typically in the range 120.° to 240.° C.

The reaction mixture may then be passed to a simultaneous saccharification and fermentation (SSF) stage, involving both cellulolytic enzymes and yeast cells, in which the bulk of the polysaccharides are converted to bio-alcohols and carbon dioxide. Alternatively the enzyme-mediated saccharification and the yeast-based fermentation of the resulting monosaccharides may be conducted as separate consecutive process steps. In either case, the lignin component of the original lignocellulose remains as solid particles in suspension and is almost always found to contain significant quantities of residual saccharides that have resisted the action of the enzymes and the yeast. This solid material that can be collected using a belt press, or by other means is called 'waste lignin'. A number of types of lignin exist amongst which are:
 a) hydrolysis lignin comprising lignin residues remaining after industrial treatment, using mineral acids, deconstructing the cellulose fibres to more digestible saccharides, followed by an enzymatic treatment converting these saccharides into bio-alcohols; and
 b) lignin resulting from the kraft or sulfite pulping processes.

Part of this waste lignin can be used to burn as fuel supporting the biorefinery process.

Presently, significant research efforts are being devoted to the development of efficient depolymerisation processes of waste lignin to form typically aromatic products.

The invention is directed to a method for producing a high value platform chemical, "(1S, 5R)"-6,8-dioxabicyclo [3.2.1]oct-2-en-4-one, also known as (−)-levoglucosenone, and here abbreviated as LGE, from waste lignin.

LGE is one of the few molecules from sustainable sources with a market value able to compete with current non-renewables. LGE is a versatile molecule that can serve as a chiral intermediate to the synthesis of a wide range of pharmaceuticals.[1] LGE can also be selectively isomerized into 5-hydroxymethylfurfural,[2] hereafter abbreviated as 5-HMF, which is a valuable precursor for both fuels and pharmaceuticals. Recently, a range of patents describe the conversion of LGE to 1,6-hexanediol and 1,2,6-hexanetriol.[3] These are key intermediates in the synthesis of 1,6-hexanediamine, caprolactone and caprolactam, which are used for the manufacturing of polyesters, polyamines and polyurethanes, representing multimillion tonne articles of commerce. Recently, it was also found that dihydro-LGE (dihydrolevoglucosenone) (Cyrene™) has great potential as a dipolar aprotic solvent with similar properties to N-methylpyrrolidone, commonly known as NMP, and N,N-dimethylformamide, commonly known as DMF.[4]

Few processes exist to produce LGE from biomass, polysaccharides, or biomass derivatives and only one process has been operated on a semi-commercial scale.[4] Most commonly phosphoric acid is used, but not limiting to, often in combination with a dipolar aprotic solvent such as sulfolane.[5] Also, the use of ionic liquids has been found beneficial.[6] Typically, all these methods require a high reaction temperature exceeding 250° C. A method was patented by Circa Group Ltd in which LGE is obtained from particulate lignocellulosic material using a polar organic liquid and a mineral acid, in the presence or absence of water, at high temperature.[7] In the Circa patent the term "lignocellulosic material" and forms of the term "lignocellulosic material" refer to materials having a combined cellulose and hemicellulose content above 30% w/w.

SUMMARY OF THE INVENTION

In a first aspect of the present invention there is provided a method of producing LGE comprising, heating lignin to a temperature in excess of 150° C. for a time sufficient to convert a proportion of the lignin to LGE.

It is preferred that the lignin contains no more than 40% w/w, more preferably no more than 30% w/w of polysaccharides.

Suitably the temperature used in the method of the invention is below 220° C., preferably below 180° C. Suitably the temperature used in the method of the invention is in the range of from about 150° C. to about 400° C. More suitably it may fall within the range of from about 150° C. to about 220° C. Even more suitably, the temperature may be in the range of from about 160° C. to about 200° C.

Suitably, the lignin is in the form of waste lignin comprising lignin rich solid residues remaining after industrial pre-treatment.

The heating of the lignin as herein described may be carried out for a time sufficient to convert at least 1% w/w of the lignin into LGE. More suitably at least 3% w/w of the lignin may be converted into LGE and most suitably at least 5% w/w of the lignin may be converted into LGE.

The heating may be carried out using any conventional heating processes. However heating by microwave radiation is preferred.

Where the heating is carried out by microwave radiation, the heating should be carried out for sufficient time to drive off volatile materials that are in admixture with the lignin, bearing in mind that waste lignin may typically also form by-product volatile materials such as acetic acid and furfural in addition to water under these conditions. After evolution of the volatile materials the lignin mix may be increased in temperature up to a target temperature such as about 160° C. to about 200° C., until there has been sufficient reaction of the lignin to produce LGE e.g. a conversion of 3% w/w of the lignin or 5% LGE w/w of the lignin.

Depending upon, inter alia, the progress of the reaction during the heating, heating may stop once the target temperature has been reached.

After completion of the reaction the resulting mix of compounds containing lignin and LGE may be cooled and the LGE may be removed.

The LGE may be harvested or removed by a solvent extraction process. Solvents which may be mentioned include non-polar solvents, such as, ethyl acetate, methyl ethyl ketone, acetone, hexane, methyl isobutyl ketone and toluene. A suitable solvent may comprise acetone or ethyl acetate.

Alternatively, other methods of removing the LGE from the reaction mixture may be used. For example, the LGE may be evaporated under reduced pressure or high temperature steam may be used to drive off the volatile LGE.

In order to ensure a substantially even or uniform reaction of the lignin, which may be in the form of waste lignin, agitation of the lignin may be carried out whilst heating occurs. Agitation may be by conventional means such as a fluidised bed, a vibrator, stirrer and/or any combination of these.

The reaction may be carried out at atmospheric pressure, super atmospheric pressure or reduced pressure in the absence or presence of air.

The waste lignin may be hydrolysed lignin, lignin resulting from other polysaccharide depleting processes and/or mixtures of these. It may typically have been prepared by heating a lignocellulosic material in an aqueous mixture having a pH less than 1, preferably at a temperature of about 120° C. to about 240° C., optionally under pressure, for a period sufficient to convert a substantial proportion of the hemicellulose material to a mixture of glucose, mannose, galactose, xylose, arabinose and glucuronic acid, and treating the resulting mixture with an enzyme to convert a substantial portion of exposed cellulose into glucose, leaving lignin with embedded and exposed crystallites of unconverted cellulose.

When the reaction is carried out at less than atmospheric pressure, it may be carried out at less than 900 millibar.

Desirably, the method produces a bio-oil from waste lignin, the bio-oil having a minimum content of 70% w/w (−)-levoglucosenone, preferably a minimum content of 90% w/w (−)-levoglucosenone.

According to a further aspect of the invention there is provided (−)-levoglucosenone prepared according a method as herein described.

According to a yet further aspect of the invention there is provided the use of (−)-levoglucosenone prepared according to the methods described herein in the preparation of dihydrolevoglucosenone.

According to a further aspect of the invention there is provided dihydrolevoglucosenone prepared using (−)-levoglucosenone; said (−)-levoglucosenone being prepared according to the methods described herein.

Methods of preparing dihydrolevoglucosenone from (−)-levoglucosenone are known to the person skilled in the art, for example, such methods are described by Sherwood et al in reference 4 herein.

The method of the present invention may have a number of advantages over known methods:

1) LGE can be obtained from a major waste lignin source, estimated at 50 million tonnes per annum.
2) LGE can be obtained from a major waste hydrolysed lignin containing a combined hemicellulose and cellulose content, e.g. less than 30% w/w.
3) The reaction does not require an organic solvent, such as sulfolane
4) The method can make use of organic and inorganic compounds already present in the waste lignin source.
5) The method can be operated at a temperature below 200° C.
6) Our method also produces a purer lignin potentially generating further added value.
7) Any type of heating could be applied be it thermal, inductive or microwave but the use of microwave heating has been found to be more efficient allowing for a lower operating temperature.

The invention will now be further explained by reference to the following example which illustrates a specific method and apparatus for performing the invention. Although the example uses a lignin-rich form of lignocellulose that is obtained as a solid waste product from various processes known in the prior art for converting the polysaccharide fraction of many types of lignocellulose by enzymatic hydrolysis into fermentable sugars and thence into ethanol and carbon dioxide, it will be apparent to one skilled in the art that many other methods of depleting the proportion of polysaccharides in lignocellulose exist. These methods include, but are not limited to, digestion with strong mineral acids, digestion for longer periods or at higher temperatures with mineral acids in dilute aqueous, or alcoholic solutions, treatment with phosphoric acid, treatment with alkanoic acids and sulfonic acids, treatment with aqueous solutions of various metal complexes that are known in the prior art to dissolve cellulose, such as copper (II) tetramine salts, copper ethylenediamine salts, cadmium ethylene diamine salts, iron (II) and iron (III) tartrate salts, mixtures of so-called 'xanthate' salts prepared by reacting aqueous solutions of sodium carbonate and various alkyl alcohols with carbon disulfide, and various tertiary amines and their zwitterions such as N-methyl morpholine N-oxide, and organic ionic liquids such as 1-butyl-3-methylimidazolium chloride and related salts.

It will be obvious to anyone skilled in the art that many industrial processes have been developed and utilised for dissolving cellulose in aqueous and organic solvents and then regenerating the cellulose as solid fibrils by extruding these cellulose solutions into a liquid medium in which cellulose is not soluble, most commonly water, or dilute aqueous acid solutions, and spinning these cellulose fibrils into regenerated cellulose yarns that can be woven, knitted, or felted into useful fabrics. Any of these methods could be used to generate a form of lignin-rich lignocellulose that could be used as the raw material for the present invention.

However the invention can be illustrated in one embodiment by using a specific type of lignin-rich lignocellulose that is commonly generated as a so-called 'hydrolysis lignin' by processes designed to convert agricultural residues, forestry residues and other forms of inexpensive, widely available lignocellulosic materials into fuel alcohols, such as bioethanol and biobutanol. Presently the hydrolysis lignin has very limited uses and a low value stemming from its use as a solid fuel, or an animal feed supplement with low nutritional value. The present invention enables high yields of a valuable and desirable chemical, levoglucosenone, to be made from residual polysaccharides present in this 'waste lignin' while leaving behind a much purer form of carbohydrate depleted lignin with very little reduction in the fuel value, or the nutritional value of this by-product.

The present invention will now be described by way of example only with reference to the accompanying figures in which:

FIG. 1 illustrates a TG-IR analysis of waste lignin.

EXAMPLE 1

Spruce sawdust was pre-treated for making waste lignin by taking spruce sawdust (1,000 kg, 0.1-3 mm) particle size and mixing it with 0.051 M aqueous sulfuric acid (3,000 L) and passing this mixture through a heated screw pressure reactor at 190° C. with a residence time of 180 seconds. The pre-treated sawdust suspension was discharged from the reactor directly into a flash tank equipped with a heat exchanger where the steam flashing off at atmospheric pressure carried away most of the volatile inhibitory compounds, such as spruce terpenes and furfural. The residual suspension was pumped to a tank containing 25,200 L 0.012 M aqueous sodium hydroxide equipped with an efficient mechanical stirrer. The suspension was pumped through a series of tubular heat exchangers to adjust the temperature of the suspension to 45° C. The suspension was pumped into a 50 cubic metre batch fermenter equipped with cooling coils and the pH was adjusted to pH 5.0 by addition of 4M sodium hydroxide solution. Diammonium hydrogen phosphate (2.35 kg) was dissolved in the suspension and cellulase (5.6 kg CTec2, Novozymes A/S) and xylanase (0.6 kg HTec2, Novozymes A/S) enzymes mixed with an inoculum of *Saccharomyces cervisiae* Strain BY4742 were added to the suspension. Stirring was continued for 96 hours while the temperature of the broth was maintained at 45-50° C. At the end of the incubation period the suspension was pumped onto a filter press and filtered to remove solid particulate waste lignin and the filtrate was collected and pumped to a falling film evaporator for extraction of ethanol in a manner that is well described in the prior art.

Physical and chemical analysis of the waste lignin revealed that it contained between 48-52 w/w % moisture and that when dried it represented 32-36% by weight of the original spruce sawdust. Chemical analysis of the dried waste lignin showed that it comprised the components shown in Table 1:

TABLE 1

| Composition of the oven dried solids present in the waste lignin on an oven dry basis. | | |
|---|---|---|
| Component | w/w % | w/w % |
| Sulfuric acid | 2.0 | |
| Acid insoluble Lignin | 77.3 | |
| Insoluble cellulose and hemicelluloses | 10.6 | |
| made up of: Glucose | | 5.27 |
| Mannose | | 3.60 |
| Glucuronic Acid | | 0.71 |
| Fucose | | 0.20 |
| Xylose | | 0.13 |
| Arabinose | | 0.09 |
| Soluble Saccharides | 11.2 | |
| made up of: Glucose | | 5.04 |
| Cellobiose | | 6.05 |
| Cello-oligomers | | 0.11 |

A portion (50 mg) of the oven-dried waste lignin obtained as described above was placed in a thermogravimetric instrument (TG—Netzsch STA 409 cell and TASC 414/3 controller attached to a Bruker Equinox 55 FT-IR spectrophotometer. The thermograms were recorded using a heating rate of 10° C. min$^{-1}$ from room temperature up to 800° C. and using a flow rate of the N$_2$ carrier gas of 100 cm$^3$ min$^{-1}$. Every 60 seconds an infrared spectrum in the region 400-4000 cm$^{-1}$ of the evolved fragments from the carbon materials was recorded.) and the volatiles produced were analysed in situ by the FT-IR spectrometer. The main volatiles were emitted around 314° C. (see TG and dTG data in FIGS. 1A and 1B) and the FT-IR spectrum at this temperature is shown in FIG. 1D. Comparative standards are shown in FIG. 1C, and demonstrate unequivocally the dominant presence of levoglucosenone in the volatile material emitted at this temperature. Quantitative analysis by GC gave an effective levoglucosenone yield of 4.2 w/w % based on the mass of the dry waste lignin analysed.

EXAMPLE 2

Waste lignin prepared as described in Example 1 was used without oven drying in this example. Waste lignin (1.4 g) was placed into a 10 mL vial and heated using microwaves (250 W in a CEM 'Discover' MW generator) to 180° C. in air. Steam formed in the process, whether coming from water already present in the waste lignin or from water formed by dehydration of saccharides, was allowed to escape from the reaction mixture. This evolution of steam typically occurs in between 90-140° C. The aqueous condensate was collected and prevented from returning to the reaction mixture. It comprised, as determined by GC-MS analysis, acetic acid and furfural in addition to water. When the target temperature of 180° C. was reached the reactor and vial were cooled to room temperature. The resulting solid material was extracted three times with acetone (3×50 mL) and the acetone solution was decanted and filtered through a sintered glass disk to remove suspended particulate solids. The acetone was evaporated under vacuum using a Rotavap evaporator at room temperature leaving an orange-brown oil (0.63 g). The oil was analysed quantitatively by GC and found to contain 90% w/w levoglucosenone. These data correspond to a levoglucosenone yield of 8% w/w based on dry waste lignin and a 37% w/w yield based on total saccharides in the waste lignin. The main by-products of this process were found to be furfural and acetic acid.

Fractional vacuum distillation of 6.3 g of the orange-brown oil at 10 kPa gave a pale yellow liquid (5.1 g) boiling over the range 120-122° C. that was found by GC analysis to contain 99.6% w/w levoglucosenone.

EXAMPLE 3

This example serves to show the efficacy of the present invention by demonstrating that lignocellulosic materials that are not depleted in saccharides by some pre-treatment by contrast do not give appreciable yields of the valuable compound levoglucosenone. A sample (1.4 g) of the same spruce sawdust used as the raw material in Example 1 was mixed with a solution of sulfuric acid (0.028 g) dissolved in water (5.0 mL) and allowed to stand for 24 hours to ensure that the water and acid had permeated through the wood matrix. The damp acidified sawdust was then placed in a 10 mL vial and irradiated with microwaves under the same conditions as specified in Example 2 until the temperature of the residual solid reached 180° C. Removal of this solid from the vial and identical extraction of the solid with acetone afforded, after solvent removal a brown viscous oil (0.24 g) that was analysed by GC and found to contain 0.05% w/w levoglucosenone, representing only 0.012% w/w yield of levoglucosenone based on the mass of saccharides present in the spruce sawdust.

EXAMPLE 4

It is possible to take aqueous solutions of lignin at high pH that are produced as a by-product of the kraft and soda pulping processes and, by adjusting the pH of the solution to lower values with an acidulant, typically waste carbon dioxide gas, to precipitate the so-called 'black liquor' lignin onto lignocellulose and/or cellulose fibres added to the solution. In this way one form of 'waste lignin' typically containing 20-30% lignocellulose or cellulose may be produced. This may comprise an alternative source of lignin for producing levoglucosenone as per Example 2.

EXAMPLE 5

The typical industrial sulphite pulping processes generate a by-product stream containing lignosulfonates dissolved in water. By adding lignocellulose and/or cellulose fibres, the pH of the suspension may be adjusted by addition of an acidulant to precipitate the a proportion of the lignosulfonates onto the fibres to create another form of 'waste lignin' containing 20-30% lignocellulose and/or cellulose that may also be used as described in Example 2 for making levoglucosenone.

EXAMPLE 6

This Example generally describes broad conditions for producing lignin suitable for use in Example 2. Sawdust or fine woodchips made from softwood or hardwood timber, cereal straw, sugar cane bagasse, or other forms of lignocellulosic materials are mixed with low pressure steam typically at 120° to 160° (e.g. about 130° C.) in a steaming vessel of a type commonly used in the chemical wood pulping industry.

The steamed lignocellulose is fed by a screw feeder at the base of the pre-steaming vessel into the inlet of a high-pressure screw feeder of a type commonly used in the chemical pulping industry for feeding wood chips into the initial stage of a kraft pulping process. The feeder is equipped with inlets to allow the injection of dilute aqueous acid such that the steamed lignocellulose is mixed with two to six times its weight of a liquid made from 0.1-1.0% w/w sulfuric acid, hydrochloric acid, phosphoric acid, or other strong mineral acid and 90.0-99.9% w/w water. The suspension is heated and to between 170-220° C. and subjected to compression and shearing as it passes along the length of the screw feeder.

The rate of rotation of the screw may be adjusted such that the lignocellulose is held for 2-4 minutes at 190° C., or for such other period of time as may be calculated to deliver an equivalent amount of thermal energy to the lignocellulose.

The outlet of the screw feeder is arranged so that the suspension of lignocellulose is discharged into a tank suitably at atmospheric pressure. The tank is equipped with a means of heat exchange that enables the steam flashing off as it exits the screw to condense on the walls of tubes, or plates through which the incoming dilute acid passes before it is brought into contact with the lignocellulose. In this way the incoming dilute acid is heated before it is injected into the screw feeder thereby saving energy.

The tank into which the acidified hot lignocellulose falls is equipped with a means of efficient mixing and a means of adding sufficient aqueous alkali to adjust the pH of the suspension to a value which is optimal for subsequent treatment by cellulolytic and hemicellulolytic enzymes—typically between values of 4.5-5.0 and a solids concentration of between 10-30% w/w.

The resulting suspension of lignocellulose is cooled to the temperature optimum activity of the mixture of cellulolytic and hemicellulolytic enzymes employed and is then either: in the case of sequential enzymatic hydrolysis and fermentation:

(a) pumped to an enzymatic hydrolysis (saccharification) vessel equipped with a means of maintaining the temperature at the optimum for enzyme activity and an efficient means of low shear mixing. The suspension in the tank is stirred until a sample of the liquid medium withdrawn from the suspension analyses for 85-90% of the expected theoretical yield of reducing sugars;

(b) the suspension containing reducing sugars, enzymes, and waste hydrolysis lignin in suspension is then pumped onto a filter press, or other suitable means of separating the suspended waste hydrolysis lignin from the aqueous solution of reducing sugars and enzymes and the filter cake of wet hydrolysis lignin containing 40-70% w/w liquid is allowed to drop into a container from where it can be conveyed to a means of thermal, or microwave heating for production of levoglucosenone as described in 2; and (c) the aqueous filtrate containing the reducing sugars and enzymes is then adjusted in pH to a value that is optimum for the activity of the fermentation organism to be used and pumped to a fermentation vessel where it is mixed with nutrients and inoculum by means well described in the prior art and allowed to ferment to produce a fermentation broth containing the desired product, typically ethanol, or n-butanol that can be isolated and purified by means that are well described in the prior art. OR, in the case of simultaneous saccharification and fermentation (SSF):

(d) pumped to a vessel equipped for SSF with a means of maintaining the temperature at the optimum for both enzyme activity and activity of the fermentation organisms provided with an efficient means of low shear mixing where it is mixed with cellulolytic and hemicellulolytic enzymes, nutrients and an inoculum of organisms that have optimum fermentation activity at a pH and temperature close to the optimum values of the cellulolytic and hemicellulolytic enzymes by means well described in the prior art and allowed to simultaneously saccharify and ferment. The suspension in the tank is held at the optimum temperature and stirred until a sample of the liquid medium withdrawn from the suspension analyses for 85-90% of the expected theoretical yield of desired fermentation product(s), typically ethanol, n-butanol and/or other desired fermentation products;

(e) the suspension containing fermentation product(s), enzymes, and waste hydrolysis lignin in suspension is then pumped onto a filter press, or other suitable means of separating the suspended waste hydrolysis lignin from the aqueous solution of fermentation product(s) and enzymes and the filter cake of wet hydrolysis lignin containing 40-70% w/w liquid is allowed to drop into a container from where it can be conveyed to a means of thermal, or microwave heating for production of levoglucosenone as described in 2; and (f) the aqueous filtrate containing the fermentation product(s) and enzymes is then treated by means well described in the prior art for isolating and purifying the desired fermentation products.

Whilst the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

REFERENCES

[1] Sarotti, A. M., Zanardi, M. M., Spanevello, R. A., Suarez, A. G. Recent applications of levoglucosenone as chiral synthon. Current Organic Synthesis 9(4), 439-459 (2012);

[2] Production Of 5-Hydroxymethyl-2-Furfural from Levoglucosenone; By Ritter, Joachim C.; Stauffer, Christina S. From PCT Int. Appl. (2013), WO 2013101970 A1 20130704;

[3] a) Process for preparing 1,6-hexanediol; Allgeier, Alan Martin; Ritter, Joachim C.; Sengupta, Sourav Kumar; From U.S. Pat. Appl. Publ. (2013), US 20130231505 A1 20130905;

b) Process for preparing 1,6-hexanediol; Alan Martin Allgeier, Namal Desilva, Ekaterini Korovessi, Carl Menning, Joachim C. Ritter, Sourav Kumar Sengupta; US 20130172629 A1;

c) Production of tetrahydrofuran-2, 5-dimethanol from isosorbide; Namal Desilva, Ekaterini Korovessi, Carl Menning, Joseph E. Murphy, Joachim C. Ritter, Sourav Kumar Sengupta, Christina S. Stauffer; US 20130172586;

d) Preparation of caprolactone, caprolactam, 2,5-tetrahydrofuran-dimethanol, 1,6-hexanediol or 1,2,6-hexanetriol from 5-hydroxymethyl-2-furfuraldehyde; Vries Johannes Gerardus De, Teddy, Phua Pim Huat, CABRERA Ignacio Vladimiro MELIÁN, Hero Jan Heeres; WO 2011149339 A1;

[4] Sherwood J., De bruyn M., Constantinou A., Moity L., McElroy C. R., Farmer T. J., Duncan T., Raverty W., Hunt A. J. and Clark J. H. Dihydrolevoglucosenone (Cyrene) as a bio-based alternative for dipolar aprotic solvents, *Chem. Commun.*, 50, 9650-9652 (2014);

[5] H. Kawamoto, S. Saito, W. Hatanaka and S. Saka; Catalytic pyrolysis of cellulose in sulfolane with some acidic catalysts; J Wood Sci (2007) 53:127-133;

[6] Kudo S., Zhou Z., Norinaga K. and Hayashia J.-I. Efficient levoglucosenone production by catalytic pyrolysis of cellulose mixed with ionic liquid, Green Chem., 13, 3306 (2011);

[7] Court, G. R., Lawrence, C. H., Raverty, W. D. and Duncan, A. J., Method for converting lignocellulosic materials into useful chemicals EP 2449057 A1 (text from WO 2011/000030A1); EP2449057 A1, Priority date: Jul. 1, 2009, Also published as CA2764865A1, CN102471694A, CN102471694B, EP2449057A4, US20120111714, WO2011000030A1.

The invention claimed is:

1. A method of producing (−)-levoglucosenone, said method comprising, heating waste lignin using microwave radiation to a temperature of between 150° C. and 240° C. for a time sufficient to convert a proportion of the waste lignin to (−)-levoglucosenone; wherein the waste lignin contains no more than 40% w/w of polysaccharides and said waste lignin has been obtained from lignocellulosic biomass by:

treating the lignocellulosic biomass with aqueous acid;
adding cellulase CTec2 and xylanase HTec2 mixed with an inoculum of *Saccharomyces cerevisiae* BY4742 to the lignocellulosic biomass and aqueous acid to create a mixture;
incubating said mixture; and
filtering the mixture at the end of the incubation to isolate the waste lignin.

2. The method according to claim 1 wherein the heating is carried out at a temperature of below 220° C.

3. The method according to claim 1 wherein the heating is carried out until the lignin has reached a target temperature within the range of about 160° C. to about 200° C. and the heating is stopped when the target temperature is reached.

4. The method according to claim 1 wherein the (−)-levoglucosenone is harvested from the converted lignin by a solvent extraction process.

5. The method according to claim 1 wherein the lignin is waste lignin resulting from industrial processing of lignocellulosic material.

6. The method according to claim 1 wherein the lignin has been prepared by heating a lignocellulosic material in an aqueous mixture having a pH less than 1.

7. The method according to claim 5 wherein the lignin has been prepared by heating a lignocellulosic material under pressure.

8. The method according to claim 5 wherein the lignin has been prepared by heating a lignocellulosic material for a period sufficient to convert a substantial proportion of hemicellulose material to a mixture of glucose, mannose, galactose, xylose, arabinose and glucuronic acid.

9. The method according to claim 5 wherein the lignocellulosic material is treated with an enzyme to convert a substantial portion of exposed cellulose into glucose leaving lignin with embedded and exposed crystallites of unconverted cellulose.

10. The method according to claim 1 wherein the waste lignin is hydrolysed lignin.

11. The method according to claim 10 wherein the waste hydrolysed lignin is reacted at atmospheric pressure.

12. The method according to claim 10 wherein the waste hydrolysed lignin is reacted at less than 900 millibar.

13. The method according to claim 10 wherein the waste hydrolysed lignin is reacted at atmospheric pressure.

14. The method according to claim 13 wherein the waste hydrolysed lignin is reacted at less than 900 millibar.

15. The method according to claim 1 wherein the method produces a bio-oil from waste lignin with a minimum content of 90% w/w (−)-levoglucosenone.

16. A method of producing (−)-levoglucosenone, said method comprising, heating waste lignin to a temperature in excess of 150° C. for a time sufficient to convert a proportion of the waste lignin to (−)-levoglucosenone; wherein the waste lignin contains no more than 40% w/w of polysaccharides and said waste lignin has been prepared by:
    heating a lignocellulosic material in an aqueous mixture having an acidic pH;
    adding cellulase CTec2 and xylanase HTec2 mixed with an inoculum of *Saccharomyces cerevisiae* BY4742 to the lignocellulosic material and aqueous acid to create a mixture;
    incubating said mixture; and
    filtering the mixture at the end of the incubation to isolate the waste lignin.

17. The method according to claim 1 wherein the acid is residual acid.

18. The method according to claim 1 wherein the waste lignin is from different lignocellulosic sources.

19. The method according to claim 16 wherein the acid is residual acid.

20. The method according to claim 16 wherein the waste lignin is from different lignocellulosic sources.

* * * * *